US010674981B2

(12) United States Patent
Vaillant et al.

(10) Patent No.: US 10,674,981 B2
(45) Date of Patent: Jun. 9, 2020

(54) METHOD FOR CONTRAST MEDIUM INJECTION VOLUME ESTIMATION BASED ON IMAGE ANALYSIS

(71) Applicant: GENERAL ELECTRIC COMPANY, Schenectady, NY (US)

(72) Inventors: Regis Vaillant, Buc (FR); Francisco Sureda, Buc (FR)

(73) Assignee: GENERAL ELECTRIC COMPANY, Schenectady, NY (US)

(*) Notice: Subject to any disclaimer, the term of this patent is extended or adjusted under 35 U.S.C. 154(b) by 319 days.

(21) Appl. No.: 15/536,600

(22) PCT Filed: Dec. 3, 2015

(86) PCT No.: PCT/US2015/063782
§ 371 (c)(1),
(2) Date: Jun. 16, 2017

(87) PCT Pub. No.: WO2016/099930
PCT Pub. Date: Jun. 23, 2016

(65) Prior Publication Data
US 2017/0347983 A1   Dec. 7, 2017

(30) Foreign Application Priority Data
Dec. 19, 2014   (GB) .................................. 1422742.5

(51) Int. Cl.
*A61B 6/00*   (2006.01)
*A61B 6/12*   (2006.01)

(52) U.S. Cl.
CPC ............ *A61B 6/481* (2013.01); *A61B 6/5217* (2013.01); *A61B 6/12* (2013.01); *A61B 6/469* (2013.01)

(58) Field of Classification Search
USPC ........................................... 382/128; 600/413
See application file for complete search history.

(56) References Cited

U.S. PATENT DOCUMENTS 5,840,026 A * 11/1998 Uber, III .................. A61B 8/06
600/431
2005/0070848 A1   3/2005 Kim et al.
(Continued)

FOREIGN PATENT DOCUMENTS

| JP | 2013540906 A | 11/2013 |
| JP | 2014144348 A | 8/2014 |
| WO | 2012127339 A1 | 9/2012 |

OTHER PUBLICATIONS

International Search Report and Written Opinion for PCT/US2015/063782, dated Mar. 21, 2016, 14 pages.
(Continued)

Primary Examiner — Nicole F Lavert
Assistant Examiner — Nicole F Johnson
(74) Attorney, Agent, or Firm — Fletcher Yoder, P.C.

(57) ABSTRACT

A computer implemented method for estimating the volume of a medium comprising a contrast agent injected to a hollow organ through a catheter during an injection event, the method comprising the determination of the duration of injection during the injection event, the determination of the flow rate based on the procedure type, acquisition type, organ, specificities of the user controlling the injection, patient characteristics, concentration of an contrast agent in the medium, administration route, type of catheter, the size of the catheter, and/or any pre-sets provided, and the calculation an estimate for the volume of medium injected based on the duration of injection and the flow rate.

8 Claims, 6 Drawing Sheets

(56) References Cited

U.S. PATENT DOCUMENTS

| | | |
|---|---|---|
| 2006/0140336 A1 | 6/2006 | Russinger et al. |
| 2013/0034278 A1* | 2/2013 | Gindele .................... G06T 7/11 |
| | | 382/128 |
| 2013/0211247 A1 | 8/2013 | Kalafut |
| 2014/0029822 A1 | 1/2014 | Cialdea, Jr. et al. |
| 2016/0263309 A1* | 9/2016 | Kalafut ................ A61M 5/007 |

OTHER PUBLICATIONS

Combined Search and Exam Report for corresponding GB Appln. No. 1422742.5, dated Jun. 22, 2015, 6 pages.

\* cited by examiner

METHOD FOR CONTRAST MEDIUM INJECTION VOLUME ESTIMATION BASED ON IMAGE ANALYSIS

CROSS-REFERENCE TO RELATED APPLICATIONS

This application is a US National Phase filing under 35 U.S.C. § 371 (c) of co-pending International Application No. PCT/US2015/063782, filed on Dec. 3, 2015, which claims priority to GB Application No. 1422742.5, filed on Dec. 19, 2014; the above-referenced applications are incorporated herein by reference in their entireties.

BACKGROUND

Image analysis in general has become a valuable tool in a wide variety of medical applications such as for the diagnosis of many diseases. Depending on the medical application, use is made of certain agents detectable for the image analysis, such as contrast agents, which need to be injected to the patient in order to visualize a certain tissue or organ. While the use of these agents is crucial for certain imaging techniques, these agents might also be harmful to the patient, depending on the amount injected to the patient.

In the field of X-Ray angiography procedures, the interventional radiologist/cardiologist performing the procedure is responsible for deciding which contrast medium will provide the best images, depending on which part of the body is being imaged and the type of the procedure. This decision will be based on the patient information, such as medical history and recent examinations (hours to a few days) involving contrast media.

Commonly used contrast media such as Iodine or Gadolinium contrast media are generally very safe for patients with normal kidney function, however there is possible increased risk for patients with limited kidney function (e.g. older people, on dialysis patients, or patients which had a kidney surgery or kidney disease in the past). These risks might include:

Severe allergic reaction,
Contrast Induced Nephropathy: It can result in temporary, prolonged or permanent worsening of kidney function which could result in the need for temporary or permanent dialysis in the most severely affected patients.

To reduce these risks, there is a maximum recommended amount of contrast agent that the patient should receive during the procedure. Other than the patient medical history, this maximum depends on the size, weight and age of the patient.

Although the amount of contrast agent injected can be captured and displayed in a computerized injector system, today the manual syringe injections remain untracked during the procedure, as they are usually tracked manually by an operator when a bottle of medium comprising the contrast agent is finished or at the end of the exam. This manual tracking however is both error-prone and imprecise. Furthermore, as the manual tracking normally is merely based on counting the used bottles of medium, no real timetracking of the volume of medium injected to the patient is possible.

Accordingly, continuous monitoring of the contrast volume delivered during the procedure is important in order to take the appropriate decision that balances clinical outcomes and quality of care, mainly on contrast-sensitive patients.

Thus, there is the need for an automatic and reliable monitoring functionality applicable to manual injection events during the procedure.

SUMMARY OF THE INVENTION

At least one of the embodiments of the present disclosure provides one or more solutions to the problems and disadvantages with the background art. Other technical advantages of the present disclosure will be readily apparent to one skilled in the art from the following description and claims.

In one aspect, the present disclosure is directed to computer implemented method for estimating the volume of a medium comprising a contrast agent injected to a hollow organ through a catheter during an injection event, the method comprising:
  determining the duration of injection during the injection event;
  determining the flow rate based on the procedure type, acquisition type, organ, specificities of the user controlling the injection, patient characteristics, concentration of an contrast agent in the medium, administration route, type of catheter, the size of the catheter, and/or any pre-sets provided; and
  calculating an estimate for the volume of medium injected based on the duration of injection and the flow rate.

In another aspect of the present disclosure, the step of determining the duration of injection comprises:
  acquiring a sequence of consecutive images of a region of injection;
  detecting a region of interest (ROI) at the tip of the catheter;
  determining a contrast profile at the ROI along the sequence of consecutive images;
  determining the duration of injection based on the contrast profile.

In another aspect, the present disclosure is directed to a computer implemented method for estimating the volume of a medium comprising a contrast agent injected to a hollow organ through a catheter during an injection event, the method comprising:
  acquiring a sequence of consecutive images of a region of injection;
  determining the duration of injection during the injection event; and
  determining the proportion of image pixels that have been effected by the presence of contrast agent,
wherein the injection event is classified based on the injection duration and on the proportion of affected image pixel into predefined injection categories, and the volume injected during the injection event is estimated based on the volume associated to the respective injection category.

In yet another aspect of the disclosure, the volume associated to the different injection categories is predefined according to the procedure type, the acquisition type, the organ, the specificities of the user controlling the injection, the patient characteristics.

In yet another aspect of the present disclosure, the injected contrast agent is an iodine contrast agent or gadolinium contrast agent. In the method step of acquiring the sequence of consecutive images, image acquisition may be done via X-ray image acquisition. Moreover it is possible that the step determining the duration of injection includes detecting a second ROI in the body of catheter. Said second ROI detected at the body of the catheter may be used as a reference for the determination of the contrast profile at the first ROI detected at the tip of the catheter.

In yet another aspect of the present disclosure, if a sequence of consecutive injection events is performed, the overall volume of injected medium injected during all of the consecutive injection events is calculated based on the determined volume of the singly injections events. Said calculated overall volume of injected medium injected during all of the consecutive injection events may be displayed on a display device. Moreover, it is possible to provide a visual or acoustic signal when the overall volume of injected medium has reached a predefined threshold value.

The method can be performed in any order, for example, the determination of the flow rate can be done before acquisition of the images and/or before the step of determination of the duration of injection.

In another aspect, the present disclosure is directed to a computer program computer program product comprising program instructions for carrying out each of the method steps of the disclosure, when said product is executed on a computer.

In another aspect, the present disclosure is directed to a computer readable medium storing program instructions, which, when executed by a processor of a computer cause the computer to perform each of the method steps of the disclosure.

In another aspect, the present disclosure is directed to a system for estimating the volume of a medium comprising a contrast agent injected to a hollow organ through a catheter during an injection event, the system comprising an imaging unit comprising an X-ray source and a detector configured to acquire a sequence of consecutive images of a region of injection, and a processing unit, the processing unit being configured to determine the duration of injection during the injection event, to determine the flow rate based on the procedure type, acquisition type, organ, specificities of the user controlling the injection, patient characteristics, concentration of an contrast agent in the medium, administration route, type of catheter, the size of the catheter, and/or any pre-sets provided, and to calculate an estimate for the volume of medium injected based on the duration of injection and the flow rate.

In yet another aspect, the present disclosure is directed to a system for estimating the volume of a medium comprising a contrast agent injected to a hollow organ through a catheter during an injection event, the system comprising an imaging unit comprising an X-ray source and a detector configured to acquire a sequence of consecutive images of a region of injection, and a processing unit, the processing unit being configured to determine the duration of injection during the injection event, to determine the proportion of image pixels that have been effected by the presence of contrast agent in the images of the sequence of consecutive images, to classify the injection event based on the injection duration and on the proportion of affected image pixel into predefined injection categories, and to estimate the of volume injected during the injection event is based on the volume associated to the respective injection category.

In yet another aspect of the disclosure the processing unit of the system may further be configured to detect a region of interest (ROI) at the tip of the catheter in an image of the sequence of consecutive images, to determine a contrast profile at the ROI at the tip of the catheter along the sequence of consecutive images, and to determine the duration of injection based on the contrast profile.

One advantage that may be realized in the practice of some embodiments of the described methods is that the amount of a contrast agent manually injected to a patient can be continuously monitored. Other technical advantages of the present disclosure will be readily apparent to one skilled in the art from the following description and claims. Various embodiments of the present application obtain only a subset of the advantages set forth. No single advantage is critical to the embodiments. Any claimed embodiment may be technically combined with any other claimed embodiments.

BRIEF DESCRIPTION OF THE DRAWINGS

The accompanying drawings illustrate exemplary embodiments of the disclosure and serve to explain, by way of example, the principles of the disclosure.

It should be noted that these Figures are intended to illustrate the general characteristics of the methods utilized in certain embodiments. However, the Figures may not precisely reflect the precise structure or performance characteristic of any given embodiment. Moreover, in the figures like reference numerals designate corresponding parts throughout the different views or embodiments.

DETAILED DESCRIPTION

The present disclosure includes multiple aspects for the estimation of the volume of an injected medium comprising a contrast agent based on image analysis, especially based on the analysis of images acquired based on X-ray acquisition. As described in more detail below, methods according to embodiments of the present invention may be used during medical procedures, where a contrast agent detectable by a corresponding image acquisition method as known to the person skilled in the art is injected to a patient for visualization of a tissue or organ by the respective imaging technique. For example, the methods according to embodiments of the present invention may be used during X-ray angiography, wherein a contrast agent detectable via X-ray technology, such as Iodine or Gadolinium contrast agent or any other suitable contrast medium known to the person skilled in the art, is injected making use of a catheter into a hollow organ of a patient. Due to the injection of the contrast agent in the hollow organ, the respective hollow organ is made visible due to the contrast caused by the agent in the acquired X-ray image. The term "hollow organ" is understood to mean any kind of visceral organ that forms a hollow tube or pouch, such as blood vessels as arteries and veins, the stomach or intestine, or that includes a cavity, like the heart or urinary bladder. The injection of the respective medium comprising the contrast agent may be performed making use of a catheter or any other suitable injection device known to the person skilled in the art. Once the medium comprising the contrast agent is injected, in the acquired image, not only pixels showing the catheter are affected by the presence of the contrast medium, but also pixels showing the respective hollow organ, e.g. an artery become affected by the presence of the contrast medium. Accordingly, the presence of the respective contrast agent in the hollow organ can be detected as a consequence of the injection event. Due to the general movement of liquid in the hollow organ, the injected medium is moved and distributed. Accordingly, after finishing the injection procedure, i.e. after the single injection event is terminated and injection of the medium into the hollow organ has stopped, contrast agent is moved and distributed and consequently removed from the place of injection an absence of the respective contrast agent in the hollow organ, or at least at the injection place, can be detected as a consequence of the injection event having stopped. A technical effect of performing the methods according to the embodiments of the disclosure is to keep track of the volume of medium comprising a contrast agent injected to a patient, especially when the injection is performed manually and in cases of multiple consecutive injection events. Manual injection is understood as injection based on manual delivery of the medium by the practitioner and automatic injection is understood as automatic injection delivered by an injector system which may be triggered by the imaging system, e.g. the X-Ray system.

Figure 1:
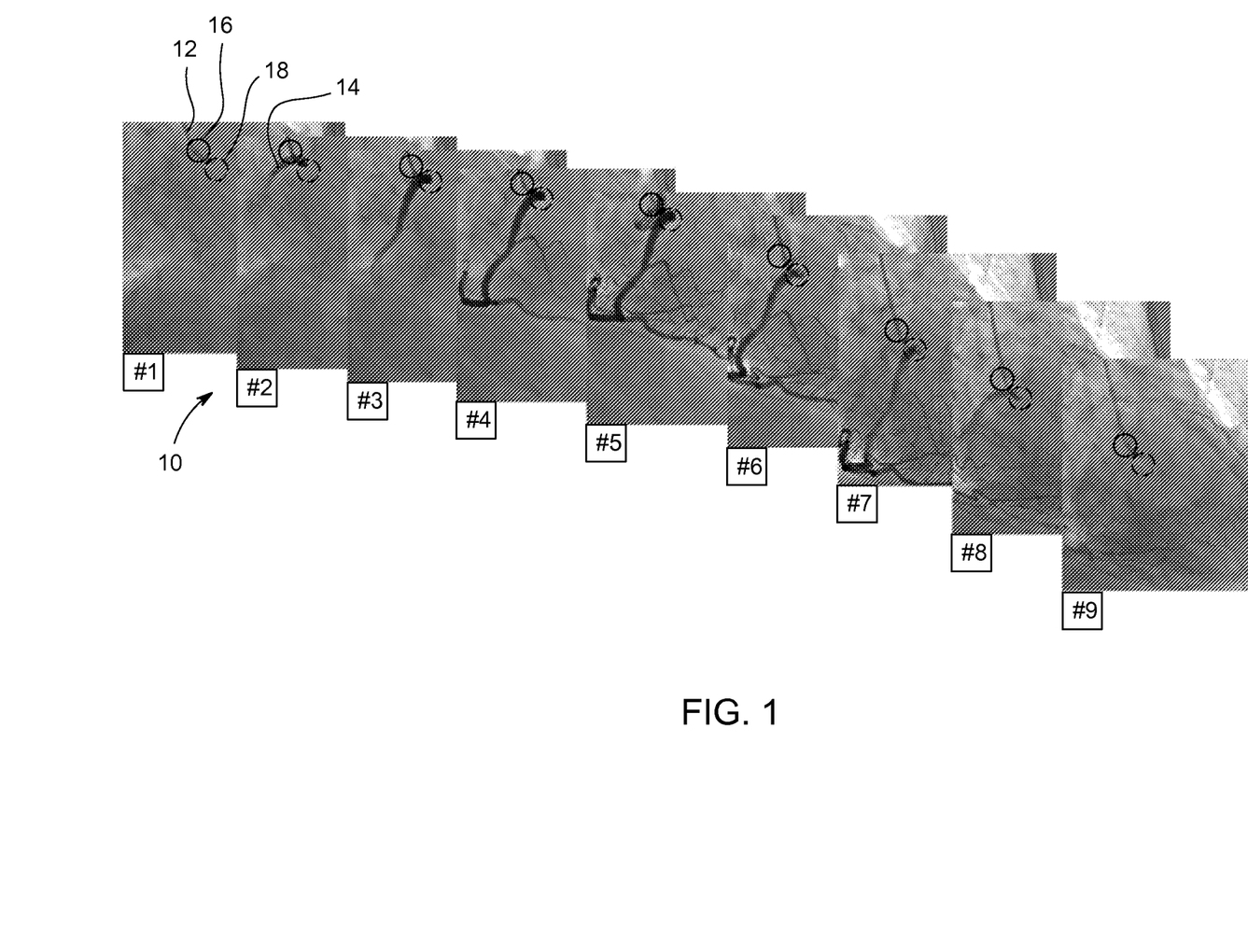
FIG. 1 shows a sequence of consecutive images of the injection area used for image analysis.

Referring now to FIG. 1 showing a sequence of consecutive images 10 of the region of injection covering the entire time of the injection event as well as the situation before onset and after termination of the injection. The medium is to be injected into a hollow organ 14, i.e. an artery in this case, making use of a catheter 12. In image #1 the catheter 12 is positioned in the artery 14 to which the contrast medium is to be injected. Upon onset of the injection, the artery 14 is filled from the catheter 12 with the medium comprising the contrast agent. The amount of medium injected per time unit depends on the flow rate. As a consequence of the injection, in images #2 to #8, pixels in the images become affected by the presence of the contrast agent injected and as such the artery 14 becomes visible by X-ray imaging. Depending on the flow rate, the contrast agent is moved in the artery 14 and in course of the injection an increasing portion of the artery 14 becomes visible as an increasing numbers of pixels according to size and shape of the artery 14 are affected by the presence of the contrast agent.

After the injection of medium comprising the contrast agent is stopped, contrast agent is distributed and therefore removed from the injection place at the tip of the catheter 12. Consequently the number of pixels affected by the contrast agent decreases, as can be seen in images #8 and #9 as shown in FIG. 1.

Figure 7:
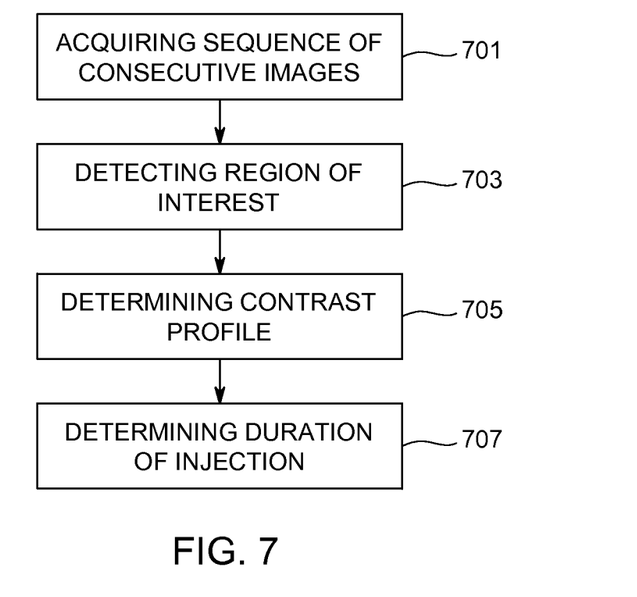
FIG. 7 shows a flow chart of the method for determining the duration of injection according to exemplary embodiments of the disclosure.

Referring now to FIG. 7 (in conjunction with FIG. 1), a flow chart of a method for determining the duration of injection according to exemplary embodiments of the disclosure is shown. For determination of the duration of an injection event, in step 701 a sequence of consecutive images 10 of the region of injection is acquired. Every image of the sequence of consecutive images 10 includes temporal information. With more detail, acquisition time of every single image is recorded and linked to the respective image to be used during further processing of the images during application of the methods according to the embodiments of the present invention. Subsequently at least one region of interest (ROI) 18, covering the catheter tip and a portion of the hollow organ where the injection takes place is detected at least one image acquired before onset of the injection. A second ROI 16 at the catheter body may be detected, to be used as a reference providing contrast values for the concentration of contrast agent present in the medium to be injected or as a reference value for the contrast caused by an empty catheter. It is understood, that detection of the ROI(s) 16, 18 may take place as soon as the first image is acquired and that the location of the ROI(s) 16, 18 may be fixed or moving over the entire injection event and whose position(s) on the images may automatically be tracked during the injection event. The ROI(s) 16, 18 may be set automatically, for example by detecting a contrast peak caused by the presence of contrast agent in the catheter and the respective affected pixels having a certain shape corresponding to the shape of the tip of the catheter or the catheter body. Alternatively the ROI(s) 16, 18 may be set manually. The size of the ROI(s) 16, 18 may be fixed or may be set in dependence of one or several predefined parameters such as the catheter size or the size of the hollow organ the injection takes place.

Figure 2:
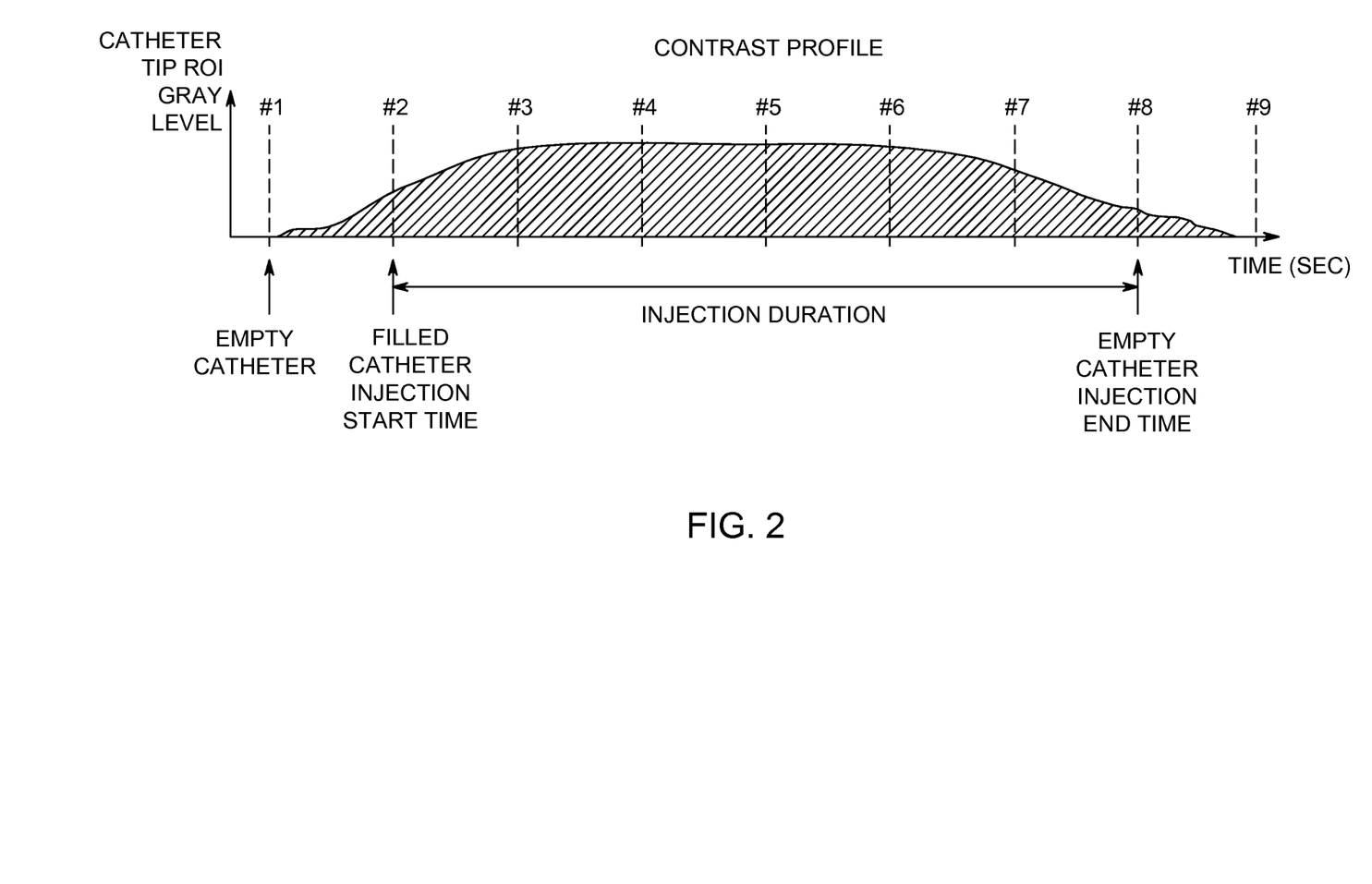
FIG. 2 shows a contrast profile based on the analysis of the sequence of consecutive images as shown in FIG. 1.

Based on the contrast detected in the ROI(s) 16, 18, i.e. the pixels affected by the contrast agent, in step 705 a contrast profile, like the one based on the ROI 18 at the catheter shown in FIG. 2 is determined. In step 707 the duration of the injection is determined based on the previously determined contrast profile. With respect to the determination of the duration, reference is also made to FIG. 1 and FIG. 2. In the contrast profile at position #2, corresponding to image #2 of FIG. 2, the contrast increases, indicating that the catheter is filled and injection has started. Accordingly, the time point of image #2 represents the start time of the injection event. Again referring to FIG. 1 and FIG. 2, when injection has stopped, the contrast detected in the ROI(s) 16, 18, i.e. the number of pixels affected by the contrast agent decreases as no further contrast agent passes through the catheter and the contrast medium already injected is moved away from the injection place. Accordingly, as shown at point #8 in FIG. 2 and can be seen in image #8 in FIG. 1, the decrease of contrast represents the end time of injection such that the duration of the injection is defined by its start time and its end time. Based on the determined start and end time of the injection and based on the temporal information linked to the images, the duration of the injection can be determined.

Figure 6:
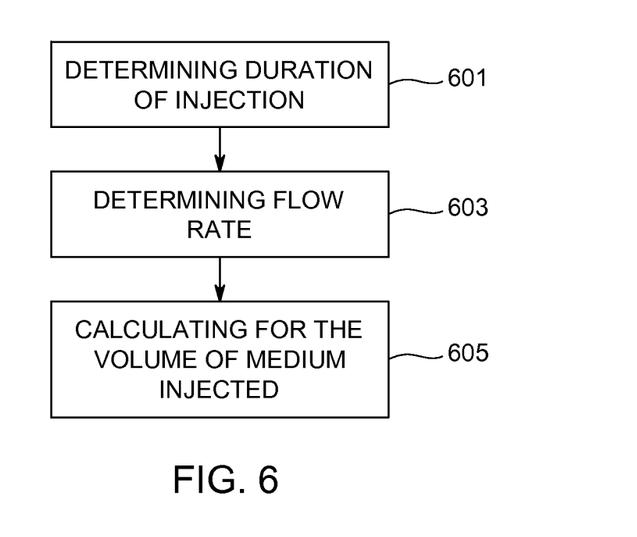
FIG. 6 shows a flow chart of the method for calculating an estimate for the volume of medium injected according to exemplary embodiments of the disclosure.

Referring now to FIG. 6, a flow chart of a method for calculating an estimate for the volume injected according to an embodiment of the invention is shown. Step 601 refers to the method for the determination of the duration of the injection as shown in FIG. 7. The volume of medium injected per time unit depends on the flow rate. The flow rate is a specific value depending on a variety of different parameters, which may include injection pressure, catheter type, catheter size, hollow organ the medium is injected to and further parameters. By the application of a model flow rate, an estimate for the flow rate, and therefore for the volume injected during a defined time interval can be given. The determination of the flow rate in step 603 may be based on different parameters like the procedure type, acquisition type, organ, specificities of the user controlling the injection, patient characteristics, concentration of a contrast agent in the medium, administration route, type of catheter, size of the catheter, and/or any pre-sets provided. Furthermore, the size of the hollow organ, e.g. the artery 14 where the injection is directed to may be determined based on the pixels in the acquired images affected by the contrast medium after onset of the injection and may be included as an additional parameter in the determination of the flow rate. In these cases, the flow rate may be re-determined and/or adapted during the procedure.

Figure 3:
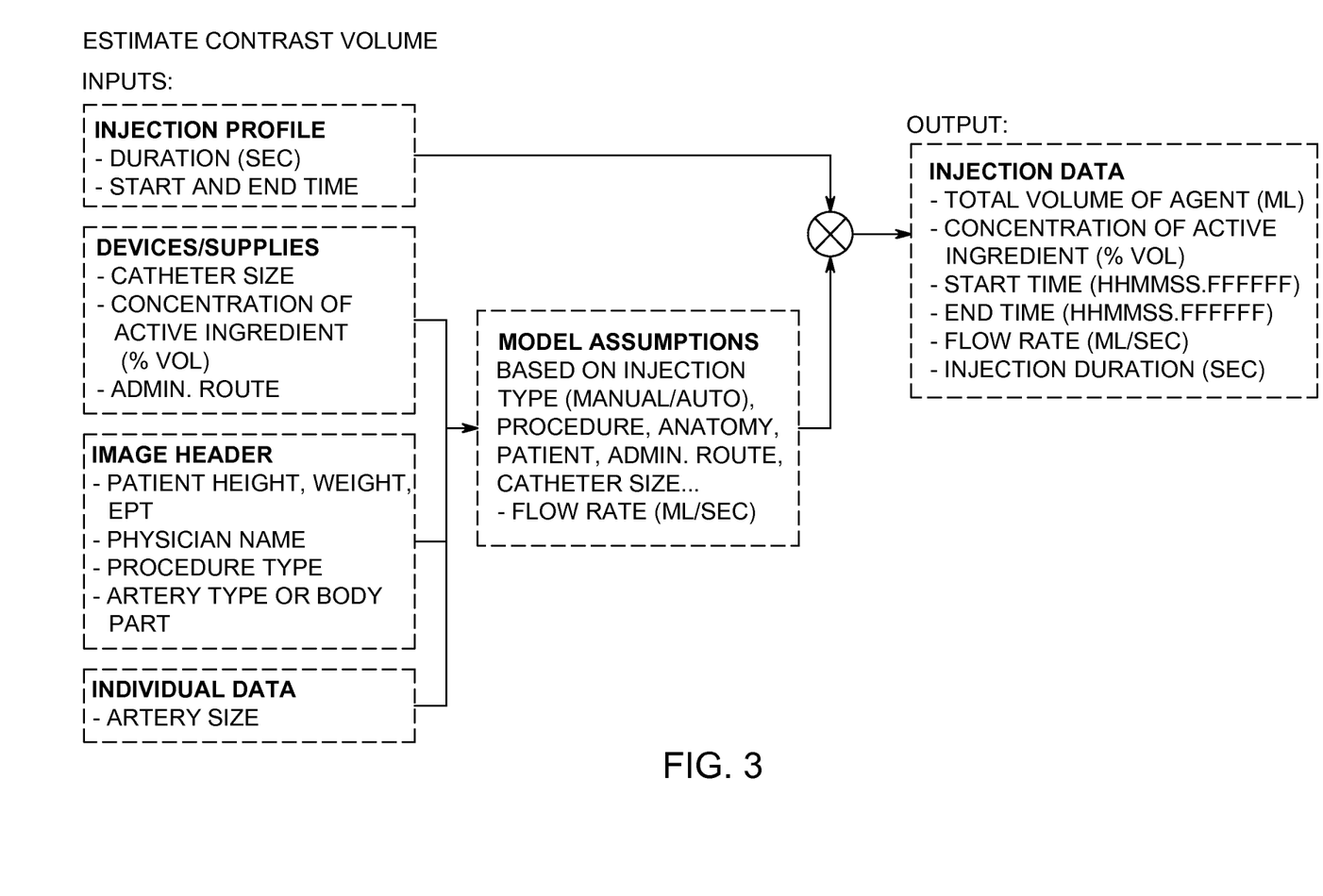
FIG. 3 shows the interrelation on processing of input data according to an exemplary embodiment of the disclosure.

Referring now to FIG. 3, a schematic overview of the interrelation of the method steps according to an embodiment of the invention is shown. A model assumption for the flow rate is determined based on certain input parameters, such as those related to the devices and the supplies used, and based on predefined parameters present in a so called image header, such as patient height and/or weight, artery type of the injection, procedure type, and based on individual data resulting from analysis of the acquired images, such as the artery. It is understood, that determination of the flow rate is not limited to the listed parameters and may also be based on a subset of the listed parameters only.

Based on the model assumption for the flow rate and based on injection profile, i.e. the duration of the injection, an output containing estimates for the injection data is provided. The output injection data may comprise the total volume of injected medium, the concentration of the contrast agent in the medium, the total amount of injected contrast agent, information regarding injection event, e.g. the start time and the end time, the injection duration, and/or the determined flow rate.

Figure 4:
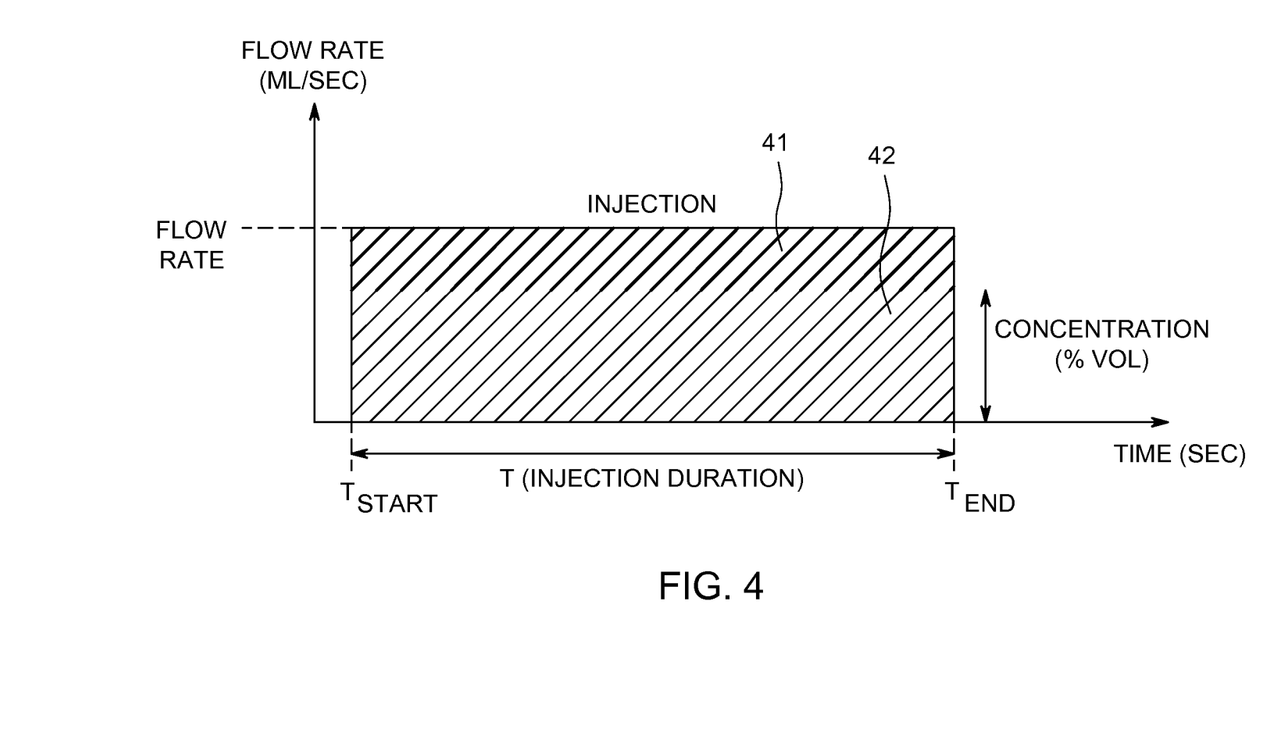
FIG. 4 shows the relation of contrast agent and active ingredient during an injection event.

Referring now to FIG. 4, a schematic view of an injection profile of an injection medium is shown comprising a certain concentration of the contrast agent, based on an injection duration T and a certain flow rate. Assuming a constant flow rate, the total amount medium 41 injected as well as the total amount of contrast agent 42 injected during an injection event can be estimated based on the information of the concentration of the contrast agent in the medium.

According to another embodiment of the invention, the estimate for the volume injected may also be acquired by:
  acquiring a sequence of consecutive images of a region of injection;
  determining the duration of injection during the injection event; and
  determining the proportion of image pixels that have been effected by the presence of contrast agent, wherein the injection event is classified based on the injection duration and on the proportion of affected image pixel into predefined injection categories, and the of volume injected during the injection event is estimated based on the volume associated to the respective injection category.

The volume associated with the different injection categories may be predefined according to the procedure type, the acquisition type, the organ, the specificities of the user controlling the injection, and/or the patient characteristics. Accordingly, different injection categories may be linked to certain values of volume injected during an injection event based on experienced data. As such the determination process may be accelerated and less computationally intensive.

Moreover, the classification process may be performed automatically based on the determination of the number of pixels affected by the contrast agent in one or more images of the sequence of consecutive images.

Figure 5:
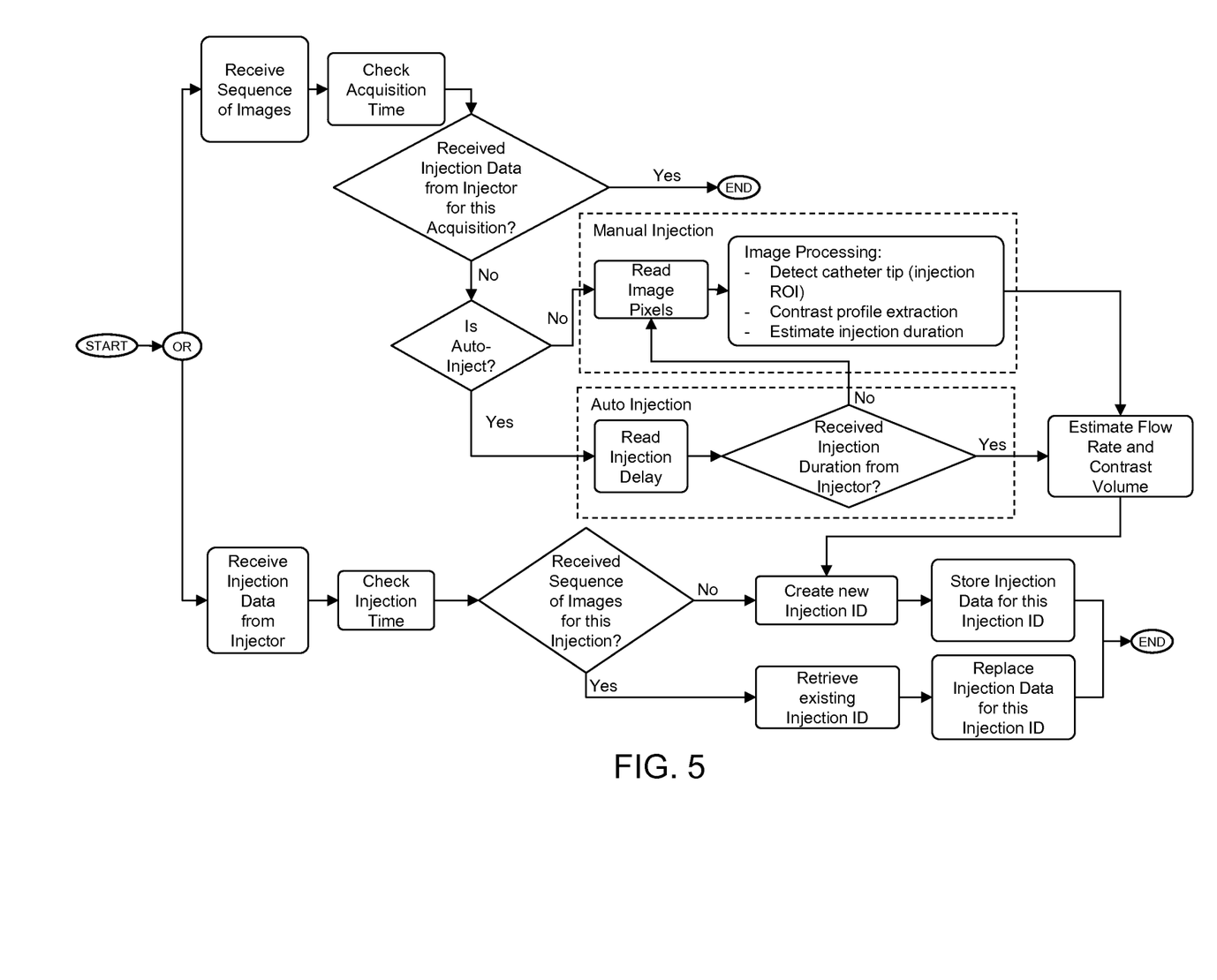
FIG. 5 shows flow charts of the method for estimating the volume of contrast agent injected according to an exemplary embodiment of the disclosure.

FIG. 5 shows a flow chart of the implementation of the methods according to the present disclosure into different injection events of the same procedure, including automatic and manual injection, to determine the volume of injected medium comprising a contrast agent. Upon reception of a sequence of consecutive images, and in case of non-reception of injector data from the injector for these images, the injection type, i.e. whether the injection is performed using an automatic injection device or whether the injection is performed manually, is determined and subsequently the volume determination is done in accordance with the injection duration time. In case that an automatic injection system is used (AUTO INJECTION), specific injector data for this injection event may be achieved and may be directly linked to the respective acquired image files because the image acquisition module and the automatic injection module are coupled to each other. In this case, the injector already provides the necessary information with respect to the injection duration and can than directly used for further processing of the data or for display.

Upon reception of injector data from the injector, image processing is not needed as the injector provides all information needed. If an estimated contrast volume, i.e. an estimate of the volume of medium injected was calculated for that injection event, it is replaced by the contrast data received from the injector. If no or insufficient injector data is available from the received image sequence, a determination whether the injection is performed using and automatic injection system or whether the injection is performed manually is made. In the first case, i.e. in case of using an automatic injection system (AUTO INJECTION), further information about the injection, such as auto-inject delay and/or duration of the injection can be gained or read out. In the second case, i.e. in case of manual injection, injection duration is determined using image analysis based on the determination of a contrast profile as described with more detail in the discussion of FIG. 6 and FIG. 7. In both cases an estimate for the volume of contrast medium injected is calculated as described in detail in the discussion of FIG. 6.

An injection identifier (INJECTION ID) is generated during every injection event. All information achieved or generated related to the single injection event is linked to the respective injection identifier. Accordingly, the estimated contrast volume, i.e. the volume of medium injected, can be linked to the injection identifier to provide the injection data of the injection event (INJECTION DATA), which can be stored for further usage, for example to be sent to another device or another instance for display or for further processing and/or storage or filing. The injection data may, in addition to the estimated or determined contrast volume parts or all of the information achieved or generated related to the single injection event, including information regarding the flow rate, comprise the equipment used, patient related date and the like.

Moreover, the contrast information of the injection event can be displayed to the practitioner performing the procedure. In addition, if a sequence of consecutive injection events is performed, the overall volume of injected medium injected during all of the consecutive injection events can be calculated based on the determined volume of the singly injections events and can be displayed in addition to the single volume to the practitioner. Moreover, it is possible to provide a visual or acoustic signal when the overall volume of injected medium has reached a predefined threshold value.

This description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art.

What is claimed is:

1. A computer implemented method for estimating a volume of a medium comprising a contrast agent injected into a hollow organ through a catheter during an injection event, the method comprising:
  determining a duration of injection during the injection event;

determining a flow rate based on a procedure type, acquisition type, organ, specificities of the user controlling the injection, patient characteristics, concentration of an contrast agent in the medium, administration route, type of catheter, a size of the catheter, and/or any pre-sets provided; and calculating an estimate for the volume of medium injected based on the duration of injection and the flow rate.

2. The method according to claim 1, wherein the step of determining the duration of injection comprises:

acquiring a sequence of consecutive images of a region of injection from a beginning of the injection event to an end of the injection event;

detecting a region of interest (ROI) at a tip of the catheter;

determining a contrast profile at the ROI at the tip of the catheter along the sequence of consecutive images; and determining the duration of injection based on the contrast profile.

3. The method according to claim 2, wherein the contrast agent is iodine contrast agent or gadolinium contrast agent.

4. The method according to claim 2, wherein the sequence of consecutive images is acquired via X-Ray image acquisition.

5. The method according to claim 2, wherein the step of determining the duration of injection further includes detecting a second ROI in a body of catheter.

6. The method according to claim 5, wherein a contrast profile detected in the second ROI is used as a reference for the determination of the contrast profile at the first ROI.

7. A non-transitory computer program product comprising program instructions for carrying out the steps of the method according to claim 1, when said product is executed on a computer.

8. A non-transitory computer readable medium storing program instructions when executed by a computer cause the computer to perform the method according to claim 1.

* * * * *